US012239685B2

(12) United States Patent
Jezek et al.

(10) Patent No.: US 12,239,685 B2
(45) Date of Patent: *Mar. 4, 2025

(54) COMPOSITION

(71) Applicant: ARECOR LIMITED, Saffron Walden (GB)

(72) Inventors: Jan Jezek, Saffron Walden (GB); David Gerring, Saffron Walden (GB); Sarah Howell, Saffron Walden (GB)

(73) Assignee: ARECOR LIMITED, Saffron Walden (GB)

( * ) Notice: Subject to any disclaimer, the term of this patent is extended or adjusted under 35 U.S.C. 154(b) by 448 days.

This patent is subject to a terminal disclaimer.

(21) Appl. No.: 17/416,677

(22) PCT Filed: Dec. 20, 2019

(86) PCT No.: PCT/GB2019/053654
§ 371 (c)(1),
(2) Date: Jun. 21, 2021

(87) PCT Pub. No.: WO2020/128506
PCT Pub. Date: Jun. 25, 2020

(65) Prior Publication Data
US 2022/0072091 A1    Mar. 10, 2022

(30) Foreign Application Priority Data

Dec. 21, 2018  (GB) .................................. 1821149
Aug. 13, 2019  (GB) .................................. 1911581

(51) Int. Cl.
| | | |
|---|---|---|
| *A61K 9/00* | (2006.01) | |
| *A61K 9/08* | (2006.01) | |
| *A61K 38/12* | (2006.01) | |
| *A61K 47/02* | (2006.01) | |
| *A61K 47/10* | (2017.01) | |
| *A61K 47/12* | (2006.01) | |
| *A61K 47/18* | (2017.01) | |
| *A61K 47/22* | (2006.01) | |
| *A61K 47/38* | (2006.01) | |
| *A61P 31/04* | (2006.01) | |

(52) U.S. Cl.
CPC ................ *A61K 38/12* (2013.01); *A61K 9/08* (2013.01); *A61K 47/02* (2013.01); *A61K 47/10* (2013.01); *A61K 47/12* (2013.01); *A61K 47/183* (2013.01); *A61K 47/22* (2013.01); *A61K 47/38* (2013.01); *A61P 31/04* (2018.01)

(58) Field of Classification Search
CPC ....... A61K 47/183; A61K 9/0019; A61K 9/08; A61K 38/28; A61K 47/10; A61K 47/12; A61K 47/26
See application file for complete search history.

(56) References Cited

U.S. PATENT DOCUMENTS

| | | | |
|---|---|---|---|
| 2002/0111311 A1 | 8/2002 | Govardhan et al. | |
| 2002/0132762 A1 | 9/2002 | Borders et al. | |
| 2006/0014674 A1 | 1/2006 | Keith et al. | |
| 2011/0124551 A1 | 5/2011 | Palepu et al. | |
| 2011/0172167 A1* | 7/2011 | Palepu .................. | A61K 47/12 514/21.1 |

FOREIGN PATENT DOCUMENTS

| | | |
|---|---|---|
| CN | 100421726 C | 10/2008 |
| WO | 02056829 A2 | 7/2002 |
| WO | 2011/035108 | 3/2011 |
| WO | 2011/062676 | 5/2011 |
| WO | 2018/073269 | 4/2018 |
| WO | 2019/043008 | 3/2019 |
| WO | 2020128507 A1 | 6/2020 |
| WO | 2020229369 A1 | 11/2020 |

OTHER PUBLICATIONS

Cubicin® (daptomycin for injection), package insert, pp. 1-32 (Mar. 2017), accessed at URL accessdata.fda.gov/drugsatfda_docs/label/2017/021572s055lbl.pdf (Year: 2017).*
Sodium chloride, ChemSpider, accessed at URL chemspider.com/Chemical-Structure.5044.html (Year: 2024).*
Qiu et al., "Evaluation of Lipopeptide (Daptomycin) Aggregation Using Fluorescence, Light Scattering, and Nuclear Magnetic Resonance Spectroscopy," Journal of Pharmaceutical Sciences, 2014, vol. 103, Issue 3, pp. 853-861, 10 pages.
International Search Report for International Application No. PCT/GB2019/053654 dated Mar. 12, 2020, 3 pages.
Ho et al., "Effect of divalent cations on the structure of the antibiotic daptomycin," European Biophysics Journal, 2007, 13 pages.
Sanchez-Rubio Ferrandez, J., et al., "Stability of daptomycin reconstituted vials and infusion solutions," Eur J Hosp Pharm., 25:107-110 (2018).

* cited by examiner

*Primary Examiner* — Julie Ha
*Assistant Examiner* — Kristina M Hellman
(74) *Attorney, Agent, or Firm* — Nixon & Vanderhye P.C.

(57) ABSTRACT

The invention provides inter alia an aqueous solution composition of pH in the range 6.0 to 8.0 comprising: —daptomycin or an analogue thereof, or a salt thereof; —a divalent metal cation; and —one or more salts which are not divalent metal cation salts or amino acid salts or buffer salts at a total concentration of 300 mM or more.

15 Claims, No Drawings

COMPOSITION

CROSS-REFERENCE TO RELATED APPLICATIONS

This is a National Stage application of PCT international application PCT/GB2019/053654, filed on Dec. 20, 2019, which claims the priority of European Patent Application No. 1821149.0, filed Dec. 21, 2018, and European Patent Application No. 1911581.5, filed Aug. 13, 2019, all of which are incorporated herein by reference in their entirety.

This invention relates to aqueous solution compositions of daptomycin, in particular containing a high salt concentration.

BACKGROUND

Daptomycin is a cyclic lipopeptide antibacterial agent derived from the fermentation of *Streptomyces roseosporus* and is produced by Merck & Co., Inc. as an antibacterial agent for use in humans under the brand name of Cubicin®. Cubicin® is supplied in a single-use vial as a sterile, preservative-free, lyophilized cake containing 350 mg or 500 mg of daptomycin for intravenous (IV) use following reconstitution with respectively 7 ml or 10 ml of sodium chloride solution (0.9%). A typical dose for an adult is 4-6 mg/kg administered once every 24 hours for 1-6 weeks according to the indication. Cubicin® should be administered intravenously either by injection over a two minute period or by infusion over a thirty minute period. Cubicin® is indicated for the treatment of the complicated skin and skin structure infections (cSSSI), and for the treatment of *Staphylococcus aureus* bloodstream infections (bacteremia).

Lyophilized daptomycin is reconstituted shortly before use because in currently available formulations, once reconstituted, the daptomycin will degrade via, inter alia, hydrolysis. The need to reconstitute the lyophilised preparation of daptomycin prior to the IV injection or IV infusion is a considerable complication of the administration procedure. Therefore, developing a stable liquid composition of daptomycin is very desirable, potentially leading to a significant simplification of the administration as well as improving the safety of the delivery due to reduced likelihood of error during the complex procedure for reconstitution and preparation of the solution for infusion.

The liquid formulation of daptomycin must meet a number of criteria in order to be approved for use in humans, including:

good physical stability (i.e. minimal aggregation and no gel formation during storage and use)

good chemical stability (i.e. impurity levels within specified limits)

minimal or no injection site reaction (e.g. pain on injection, reddening of the injection site)

acceptable safety profile.

The objective of the present invention is the provision of a liquid formulation of daptomycin, particularly at high strength such as at 50 mg/ml, which has good physical and chemical stability and is suitable for intravenous use in humans, optionally following dilution.

In particular, the objective of the present invention is the provision of a stable liquid formulation of daptomycin (for example, at 50 mg/ml) that is suitable for an IV delivery (either as an IV injection or as an IV infusion).

WO2011/035108A1 and WO2011/062676A1 (both EAGLE PHARMACEUTICALS, INC.) disclose compositions containing daptomycin which are said to have long term storage stability.

WO2018/073269A1 (XELLIA PHARMACEUTICALS APS) discloses formulations comprising daptomycin, one or more polar protic solvents, and mixtures thereof.

US2002/0111311A1 (GOVARDHAN ET AL.) discloses methods of preparing daptomycin in crystalline form.

SUMMARY OF THE INVENTION

Thus, according to the present invention, there is provided an aqueous solution composition of pH in the range 6.0 to 8.0 comprising:

daptomycin or an analogue thereof, or a salt thereof;

a divalent metal cation; and one or more salts which are not divalent metal cation salts or amino acid salts or buffer salts at a total concentration of 300 mM or more.

DETAILED DESCRIPTION OF THE INVENTION

Described herein are stable aqueous solution compositions of damptomycin and a divalent cation containing a high salt concentration.

Daptomycin is a cyclic lipopeptide antibacterial agent with chemical name N-decanoyl-L-tryptophyl-D-asparaginyl-L-aspartyl-Lthreonylglycyl-L-ornithyl-L-aspartyl-D-alanyl-L-aspartylglycyl-D-seryl-threo-3-methyl-L-glutamyl-3-anthraniloyl-L-alanine ε1-lactone. Daptomycin is also known as LY 146032, and is a member of the factor A-21978$_0$ type antibacterial agents of *Streptomyces roseosporus*. The chemical structure of daptomycin is:

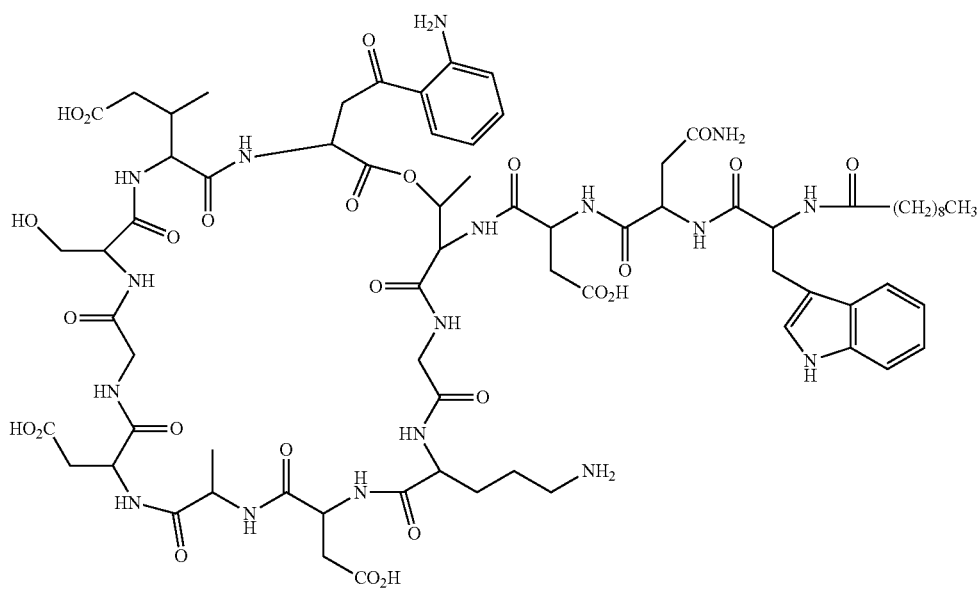

The empirical formula of daptomycin is $C_{72}H_{10}N_{17}O_{26}$ and its molecular weight is 1619.71.

Analogues of daptomycin include A-21978$O_0$ type antibacterial agents.

Salts of daptomycin and its analogues thereof may be formed with a suitable counter ion including, but not limited to, sodium, potassium, magnesium, calcium, manganese and zinc.

Compositions containing a higher concentration of daptomycin are of particular interest. Formulating aqueous peptide therapeutics at higher concentrations is challenging due to increased rate of molecular interactions between the peptide molecules. The increased molecular interactions can lead to greater rate of aggregation, fibril formation as well as other degradation pathways that are due to inter-molecular interactions.

In one embodiment, the concentration of daptomycin in the composition is >25 mg/ml, such as ≥27 mg/ml, ≥30 mg/ml, ≥35 mg/ml, ≥40 mg/ml, ≥45 mg/ml or ≥50 mg/ml. In one embodiment, the concentration of daptomycin in the composition is up to 100 mg/ml e.g. up to 60 mg/ml e.g. is 30-100 mg/ml, e.g. 30-60 mg/ml, e.g. 35-60 mg/ml, e.g. 40-60 mg/ml, e.g. 45-55 mg/ml. In one embodiment, the concentration of daptomycin in the composition is about 50 mg/ml.

The term "aqueous solution composition", as used herein, refers to a solution composition in water, preferably distilled water, deionized water, water for injection, sterile water for injection or bacteriostatic water for injection.

The composition of the invention comprises water in an amount of at least 65% (w/v), such as at least 70% (w/v), at least 75% (w/v), at least 80% (w/v), at least 85% (w/v), or at least 90% (w/v).

In one embodiment, the composition solvent comprises (based on volume) at least 80% water, such as at least 85% water, at least 90% water, at least 95% water or at least 99% water. In one embodiment, the solvent is water i.e. the only solvent present in the composition is water.

The present inventors have discovered that the adjustment of certain composition parameters and the addition of certain additives to the composition, can provide concentrated daptomycin compositions with improved chemical and/or physical stability.

Firstly, the present inventors have discovered that in certain damptomycin compositions, the presence of a divalent metal ion can improve the stability of the daptomycin. As can be seen in Example 1, both calcium chloride and magnesium chloride improved the stability of daptomycin, with calcium chloride showing the largest effect.

In one embodiment, the divalent metal cation is selected from calcium, magnesium, manganese and zinc ions. In one embodiment, the divalent metal cation is calcium ion. In another embodiment, the divalent metal cation is magnesium ion.

The divalent metal cation will typically be added to the composition in the form of a salt e.g. as a chloride salt, a nitrate salt, an acetate salt, a lactate salt or a sulfate salt. The divalent metal cation can also be added to the composition as a hydroxide.

In one embodiment, the concentration of divalent metal cation in the composition is 10-150 mM, such as 20-130 mM, 30-120 mM, 40-100 mM, 40-80 mM or 50-70 mM.

Secondly, the present inventors have discovered that in certain daptomycin compositions, optimisation of the pH can improve the stability of the daptomycin. Thus, the pH of the composition is between 6.0 and 8.0. As can be seen from Example 1, the optimal pH for daptomycin in the presence of calcium ions for the compositions tested was approximately 6.0-7.0 and thus may be around 6.0. In some instances, the optimum pH may be around 7.0, see Example 2. In a suitable embodiment, the pH of the composition is in the range 6.5 to 7.5. e.g. 6.8 to 7.2. e.g. 6.9 to 7.1 e.g. around 7.0. All references herein to "pH" refer to the pH of a composition evaluated at 25° C.

Thirdly, the present inventors have discovered that in certain daptomycin compositions, the presence of a high concentration of a salt can improve the stability of the daptomycin. As can be seen from Examples 2 and 3, use of a high concentration of sodium chloride, even as much as 2000 mM sodium chloride increased the chemical stability of the composition as compared with compositions having a sodium chloride concentration of 150 mM or containing no added sodium chloride. Higher stability was associated with higher concentrations of sodium chloride used.

Thus, the compositions of the invention comprise one or more salts which are not divalent metal cation salts or amino acid salts or buffer salts at a total concentration of more than 300 mM. For example, the total concentration of the one or more salts may typically be 350 mM or more e.g. 400 mM or more e.g. 500 mM or more e.g. 600 mM or more e.g. 700 mM or more e.g. 800 mM or more e.g. 900 mM or more e.g. 1000 mM or more e.g. 1500 mM or more. The total concentration of the one or more salts may typically be 3000 mM or less e.g. 2500 mM or less e.g. 500-3000 mM e.g. 500-2500 mM e.g. 1000-2500 mM e.g. e.g. 1500-2500 mM e.g. around 2000 mM. The concentration of daptomycin and any counterion is not counted in the calculation of the concentration of the one or more salts which are not divalent metal cation salts or amino acid salts or buffer salts.

Suitably the one or more salts which are not divalent metal cation salts or amino acid salts or buffer salts are selected from pharmaceutically acceptable salts such as inorganic salts e.g. Group 1 metal halides (especially chlorides), Group 1 metal sulfates, Group 1 metal nitrates and ammonium salts (e.g. halides). Salts may be salts with an inorganic cation or an organic anion (e.g. salts of weak acids such as lactate salts (e.g. sodium lactate) or, for example, acetate, succinate or fumarate salts (such as the sodium salts of these acids). Suitably the salts are salts of an inorganic cation and an inorganic cation. Suitable metal salts include Group 1 metals e.g. sodium and potassium, particularly sodium. Suitable halides include chlorides. The most favoured salt is sodium chloride.

Divalent metal cation salts are salts of divalent metal cations with a corresponding anion.

Suitably the one or more salts which are not divalent metal cation salts or amino acid salts or buffer salts are not zwitter ions (i.e. do not comprise both a positively charged ion and a negatively charged ion).

The one or more salts which are not divalent metal cation salts or buffer salts are also not amino acid salts. The term amino acid salts includes amino acids which comprise an equal number (e.g. one) of positively charged and negatively charged ions (for which no counter ion is necessarily required) as well as amino acids which comprise more positively charged than negatively charged ions, or vice versa, and thus require a counter ion. The term amino acid salts includes all 20 natural proteinogenic amino acids and their salts formed with counter ions.

The one or more salts which are not divalent metal cation salts or amino acid salts are also not buffer salts. Buffer salts are the salts of buffers. Buffers are substances having at least one ionisable group with a $pK_a$ which is within 2 pH units of the pH of the composition.

In an embodiment, the composition contains a single such salt. In an embodiment, the composition contains two such salts.

The present inventors have also discovered that in certain daptomycin compositions, the presence of a buffer can in some cases be tolerated at relatively low concentrations but has a detrimental impact on the stability of the daptomycin at higher concentrations. Thus Examples 1 and 4 show that certain buffers (such as phosphate and ADA) had a detrimental effect on the chemical stability of daptomycin at a concentration of 50 mM but certain buffers were tolerable at a concentration of 20 mM. Example 4 shows that histidine buffer can be deleterious to the stability of the formulation at concentrations of 10 mM or more. Example 4 also shows that ADA buffer can cause instability even at 20 mM. Thus, the concentration of buffer in the composition should suitably be limited as much as possible or avoided.

Without wishing to be bound by theory, it is thought that daptomycin, when formulated at the concentrations and pH ranges described herein, is itself a relatively good buffer. This self-buffering capacity of daptomycin means that the addition of a buffer to the composition is not essential to ensure sufficient buffering capacity. It should be noted that the "total concentration" of buffers in the compositions of the invention excludes the concentration of daptomycin in the composition. However, when calculating the concentration of buffers in the aqueous solution composition, any counterions in salt forms of daptomycin with buffering capacity should be included in the total concentration of buffers.

In one embodiment, the total concentration of buffers in the composition is 0-5 mM, such as 0-4 mM, 0-3 mM, 0-2 mM, 0-1 mM, 0-0.5 mM, 0-0.4 mM, 0-0.3 mM, 0-0.2 mM or 0-0.1 mM.

In one embodiment, the total concentration of buffers in the composition is 0.1-5 mM, such as 0.1-4 mM, 0.1-3 mM, 0.1-2 mM, 0.1-1 mM, 0.1-0.5 mM, 0.1-0.4 mM, 0.1-0.3 mM or 0.1-0.2 mM.

In one embodiment, the total concentration of buffers in the composition is 0.2-5 mM such as 0.2-4 mM, 0.2-3 mM, 0.2-2 mM, 0.2-1 mM, 0.2-0.5 mM, 0.2-0.4 mM or 0.2-0.3 mM.

In one embodiment, the total concentration of buffers in the composition is 0.3-5 mM, such as 0.3-4 mM, 0.3-3 mM, 0.3-2 mM, 0.3-1 mM, 0.3-0.5 mM or 0.3-0.4 mM.

In one embodiment, the total concentration of buffers in the composition is 0.4-5 mM, such as 0.4-4 mM, 0.4-3 mM, 0.4-2 mM, 0.4-1 mM or 0.4-0.5 mM.

In one embodiment, the total concentration of buffers in the composition is 0.5-5 mM, such as 0.5-4 mM, 0.5-3 mM, 0.5-2 mM or 0.5-1 mM.

In one embodiment, at least one buffer is present and the total concentration of buffers in the composition is ≤5 mM, such as ≤3 mm, ≤2 mM, ≤1 mM, ≤0 mM, ≤0.5 mM, 0.4 mM, 0.3 mM, ≤0.2 mM or ≤0.1 mM.

In other embodiments, total concentration of buffers in the composition is 0.1-25 mM such as 0.2-20 mM such as 0.5-20 mM e.g. 5-20 mM e.g. 5-10 mM.

In one embodiment, the composition is substantially free of buffers. As used herein, "substantially free" means the total concentration of buffers in the aqueous solution composition is less than 0.1 mM. To reiterate, when considering the concentration of buffer in the solution composition, any buffering capacity of the daptomycin itself should be excluded. In one embodiment, the composition does not contain buffer.

The buffer(s) where present will have buffering capacity at the pH of the composition.

The pH of the composition is in the range 6.0 to 8.0, and in an embodiment the composition optionally comprises one or more buffers being substances having at least one ionisable group with a $pK_a$ in the range 4.0 to 10.0 especially 4.0 to 9.0 and which $pK_a$ is within 2 pH units of the pH of the composition.

Compositions which are substantially free of buffers are suitably substantially free of substances having at least one ionisable group with a $pK_a$ in the range 4.0 to 10.0 (e.g. 4.0 to 9.0) and which $pK_a$ is within 2 pH units of the pH of the composition.

Buffers typically comprise ionisable groups with $pK_a$ within 1 pH unit of the pH of the composition, however, a moiety which has ionisable groups with p$K_a$ more than 1 pH unit greater or less than the pH of the composition may also provide some buffering effect if present in a sufficient amount. In one embodiment, the (or a) buffer comprises ionisable groups with p$K_a$ within 1 pH unit of the pH of the composition. In another embodiment, the (or a) buffer comprises ionisable groups with p$K_a$ within 1.5 pH units of the pH of the composition (such as between 1 and 1.5 pH units of the pH of the composition). In a further embodiment, the (or a) buffer comprises ionisable groups with p$K_a$ within 2 pH units of the pH of the composition (such as between 1.5 and 2 pH units of the pH of the composition). Buffering capacity is suitably determined at 25° C.

In an embodiment, the composition optionally comprises one or more buffers being substances having at least one ionisable group with a p$K_a$ in the range 5.0 to 8.0 and which p$K_a$ is within 1 pH units of the pH of the composition.

In an embodiment, the composition contains a single buffer. In an embodiment, the composition contains two buffers.

In one embodiment, the composition contains a buffer with a single ionisable group. In one embodiment, the composition does not contain zwitterionic species.

The pH of an aqueous solution decreases if an acid is added and increases if a base is added. At a given temperature and atmospheric pressure, the magnitude of the pH decrease on addition of an acid or the magnitude of the pH increase on addition of a base depends on (1) the amount of the acid or the base added, (2) the starting pH of the aqueous solution (i.e. prior to the addition of the acid or the base) and (3) the presence of a buffer. Thus, (1) starting from a given pH, the addition of a greater amount of an acid or a base will result in greater magnitude of pH change, (2) addition of a given amount of an acid or a base will result in the greatest pH change at neutral pH (i.e. pH 7.0) and the magnitude of the pH change will decrease as the starting pH moves away from pH 7.0 and (3) the magnitude of the pH change, starting from a given pH, will be smaller in the presence of a buffer than in the absence of a buffer. A buffer thus has the ability to reduce the change in pH if an acid or a base is added to the solution.

Suitably, a substance is considered to be a buffer if it is capable of reducing the magnitude of the pH change of a solution to 75%, preferably 50%, most preferably to 25%, compared with an identical solution that does not comprise the buffer, when either strong acid or a strong base is added resulting in 0.1 mM increase of the acid or the base in the solution.

Conversely, suitably, a substance is not considered to be a buffer if it is not capable of reducing the magnitude of the pH change of a solution to 75%, preferably 50%, most preferably to 25%, compared with an identical solution that does not comprise the substance, when either strong acid or a strong base is added resulting in 0.1 mM increase of the acid or the base in the solution.

In one embodiment, the or a buffer is an amino acid. In another embodiment, the or a buffer is not an amino acid.

In one embodiment, the composition comprises a buffer or buffers selected from the group consisting of maleate, sulphite, aspartame, aspartate, glutamate, tartrate, adenine, succinate, ascorbate, benzoate, phenylacetate, gallate, cytosine, p-aminobenzoic acid, sorbate, acetate, propionate, alginate, urate, 2-(N-morpholino)ethanesulphonic acid, bicarbonate, bis(2-hydroxyethyl) iminotris(hydroxymethyl)methane, N-(2-acetamido)-2-iminodiacetic acid, 2-[(2-amino-2-oxoethyl)amino]ethanesulphonic acid, piperazine-N,N'-bis(2-ethanesulphonic acid) (PIPES), phosphate, N,N-bis(2-hydroxyethyl)-2-aminoethanesulphonic acid, 3-[N,N-bis(2-hydroxyethyl)amino]-2-hydroxypropanesulphonic acid, triethanolamine, piperazine-N,N'-bis(2-hydroxypropanesulphonic acid), 2-[(2-amino-2-oxoethyl)-(carboxymethyl) amino]acetic acid (ADA), tris(hydroxymethyl)aminomethane (TRIS), N-tris(hydroxymethyl)glycine, N-tris (hydroxymethyl)methyl-3-am inopropanesulphonic acid, citrate and salts thereof, and combinations thereof. Such buffers contain ionisable groups with p$K_a$ in the range 4.0-9.0.

In one embodiment, the buffer is selected from the group consisting of maleate, tartrate, benzoate, acetate, bicarbonate, phosphate, tris(hydroxymethyl)aminomethane (TRIS) and citrate, in particular, acetate, phosphate, tris(hydroxymethyl)aminomethane (TRIS) and citrate, especially phosphate.

It should be noted that all references to "p$K_a$" refer to the p$K_a$ of an ionisable group evaluated at 25° C. (see CRC Handbook of Chemistry and Physics, 79$^{th}$ Edition, 1998, D. R. Lide).

The addition of one or more stabilizers to the composition can provide further stability benefits. A stabilizer will be employed in a stabilizing amount.

At certain pH ranges the stabilizers, or indeed any other additives described herein (including chelating agents, amphipathic species etc) may have buffering capacity, e.g. in a composition of pH in the range 6.0-8.0, the stabilizer or additive may have at least one ionisable group with a p$K_a$ in the range 4.0 to 9.0 and which p$K_a$ is within 2 pH units of the pH of the composition. For the avoidance of doubt, the concentration of such stabilizers or additives should be included in the total concentration of buffers. In an embodiment, such stabilizers or additives are therefore present in the composition at a concentration which is sufficiently low such that the total buffer concentration limitation is met e.g. does not exceed 5 mM.

In one embodiment, the stabilizer is selected from amino acids, particularly natural amino acids, such as α-amino acids. In one embodiment, the amino acid is selected from the group consisting of methionine, glycine, proline, arginine, lysine, aspartic acid and glutamic acid, and in particular is selected from the group consisting of consisting of glycine, proline, methionine, arginine, lysine and aspartic acid e.g. is selected from the group consisting of consisting of glycine, proline, methionine, arginine and lysine. Suitably, the amino acid when present is present at a concentration of 1-200 mM, such as 1-100 mM, 1-50 mM, 1-20 mM, 1-10 mM, 1-5 mM, 1-4 mM, 1-3 mM or 1-2 mM.

In one embodiment, the amino acid is not a buffer at the given pH of the composition i.e. the amino acid does not comprise ionisable groups with p$K_a$ within 2 pH units, such as 1.5 pH units or 1 pH unit of the pH of the composition. In one embodiment the amino acid is not histidine.

Although compositions of the invention will typically be hypertonic they may nevertheless comprise an uncharged tonicity modifier. Examples of uncharged tonicity modifiers include sugars (such as sucrose, trehalose and lactose), sugar alcohols (such as mannitol and sorbitol), other polyols (such as glycerol and 1,2-propanediol) and polyethylene glycols (such as PEG300 and PEG400). In one embodiment, the uncharged tonicity modifier is selected from the group consisting of glycerol, 1,2-propanediol, mannitol, sorbitol, sucrose, trehalose, lactose, PEG300 and PEG400, and particularly selected from glycerol and 1,2-propanediol. In another embodiment the uncharged tonicity modifier is not a co-solvent in the composition, for example, it is a sugar or sugar alcohol and e.g. is selected from the group consisting of mannitol, sorbitol, sucrose, trehalose and lactose. As shown in Example 2, uncharged tonicity modifiers appear to be tolerated in compositions of the invention.

The composition may optionally comprise a surfactant, suitably at a concentration of 0.01-10 mg/ml, such as 0.05-2 mg/ml.

In one embodiment, the surfactant is a non-ionic surfactant. A particularly suitable class of non-ionic surfactants is the alkyl glycosides, especially dodecyl maltoside. Other alkyl glycosides include dodecyl glucoside, octyl glucoside, octyl maltoside, decyl glucoside, decyl maltoside, tridecyl glucoside, tridecyl maltoside, tetradecyl glucoside, tetradecyl maltoside, hexadecyl glucoside, hexadecyl maltoside, sucrose monooctanoate, sucrose mono decanoate, sucrose monododecanoate, sucrose monotridecanoate, sucrose monotetradecanoate and sucrose monohexadecanoate.

Another suitable class of non-ionic surfactants is the polysorbates (fatty acid esters of ethoxylated sorbitan), such as polysorbate 20 or polysorbate 80. Polysorbate 20 is a mono ester formed from lauric acid and polyoxyethylene (20) sorbitan in which the number 20 indicates the number of oxyethylene groups in the molecule. Polysorbate 80 is a mono ester formed from oleic acid and polyoxyethylene (20) sorbitan in which the number 20 indicates the number of oxyethylene groups in the molecule. Polysorbate 20 is known under a range of brand names including in particular Tween 20, and also Alkest TW 20. Polysorbate 80 is known under a range of brand names including in particular Tween 80, and also Alkest TW 80. Other suitable polysorbates include polysorbate 40 and polysorbate 60.

Another suitable class of non-ionic surfactants is alkyl ethers of polyethylene glycol, especially those known under a brand name Brij, such as selected from polyethylene glycol (2) hexadecyl ether (Brij 52), polyethylene glycol (2) (oleyl ether (Brij 93) and polyethylene glycol (2) dodecyl ether (Brij L4). Other suitable Brij surfactants include polyethylene glycol (4) lauryl ether (Brij 30), polyethylene glycol (10) lauryl ether (Brij 35), polyethylene glycol (20) hexadecyl ether (Brij 58) and polyethylene glycol (10) stearyl ether (Brij 78).

Another suitable class of non-ionic surfactants is block copolymers of polyethylene glycol and polypropylene glycol, also known as poloxamers, especially poloxamer 188, poloxamer 407, poloxamer 171 and poloxamer 185. Poloxamers are also known under brand names Pluronics or Koliphors. For example, poloxamer 188 is marketed as Pluronic F-68.

Another suitable class of non-ionic surfactants are alkylphenyl ethers of polyethylene glycol, especially 4-(1, 1,3,3-tetramethylbutyl)phenyl-polyethylene glycol, also known under a brand name Triton X-100.

In one embodiment, the non-ionic surfactant is selected from the group consisting of an alkyl glycoside, a polysorbate, an alkyl ether of polyethylene glycol, a block copolymer of polyethylene glycol and polypropylene glycol, and an alkylphenyl ether of polyethylene glycol. In one embodiment, the concentration of the non-ionic surfactant in the composition is 10-10,000 µg/ml, such as 10-8,000 µg/ml, 10-5,000 µg/ml, 10-3,000 µg/ml, 10-2000 µg/ml, 50-1000 µg/ml, 100-500 µg/ml or about 200 µg/ml. In one embodiment, the non-ionic surfactant is an alkyl glycoside at a concentration of 10-10,000 µg/ml, such as 100-10,000 µg/ml, 1,000-10,000 µg/ml or 5,000-10,000 µg/ml.

In one embodiment, the surfactant is a cationic surfactant. Suitable cationic surfactants include benzalkonium and benzethonium salts. In one embodiment, the cationic surfactant is selected from benzethonium salts e.g. benzethonium halide such as benzethonium chloride. In another embodiment, the cationic surfactant is selected from benzalkonium salts e.g. benzalkonium halide such as benzalkonium chloride. In a further embodiment, the cationic surfactant is a mixture of benzethonium salts and benzalkonium salts such as a mixture of benzethonium chloride and benzalkonium chloride. In one embodiment, the concentration of the cationic surfactant in the composition is 10-2000 µg/ml, such as 50-1000 µg/ml, 100-500 µg/ml or about 200 µg/ml.

In one embodiment, the surfactant is an anionic surfactant. Suitable anionic surfactants include sodium dodecyl sulfate, ammonium dodecyl sulfate, carboxylate salts (sodium or ammonium salts of stearic or palitic acid), and ether phosphates.

In one embodiment, the surfactant is a zwitterionic surfactant. Suitable zwitterionic surfactants include phosphatidylcholine, phosphatidylserine, phosphatityletholamine and 3-[(3-cholamidopropyl)dimethylammonio]-1-propanesulfonate (CHAPS).

Suitably, the surfactant is a non-ionic surfactant, as described above.

In one embodiment, the composition further comprises a surfactant and an uncharged tonicity modifier e.g. selected from sugars, sugar alcohols, other polyols and polyethylene glycols.

The composition may optionally comprise an antioxidant. In one embodiment, the antioxidant is selected from the group consisting of methionine, glutathione, ascorbate, butylated hydroquinone, lactate, nicotinamide, nicotinate, tryptophan, phenylalanine and tyrosine and is suitably selected from methionine, glutathione, ascorbate and butylated hydroquinone, and in particular is methionine. Suitably, the antioxidant is present at a concentration of 1-100 mg/ml, such as 5-50 mg/ml. Without being bound by theory, it is thought that the presence of an antioxidant may improve the chemical and/or physical stability of daptomycin, for example by eliminating free radicals that may play a part in some of the degradation pathways. In one embodiment, the composition comprises two antioxidants e.g. selected from the group consisting of methionine, glutathione, ascorbate, butylated hydroquinone, lactate, nicotinamide, nicotinate, tryptophan, phenylalanine and tyrosine.

The composition may optionally comprise a chelating agent. By chelating agent is meant an agent capable of complexing with metal ions particularly ions of heavy metals such as iron or copper. Trace amounts of these metals can accelerate chemical degradation of daptomycin. Such metals can be introduced into the formulation as trace contaminants of the desirable salts of divalent metals. In one embodiment, the chelating agent is selected from the group consisting of EDTA (ethylenediaminetetraacetic acid), EGTA (ethylene glycol-bis(β-aminoethyl ether)-N,N,N',N'-tetraacetic acid) and citrate. In one embodiment the chelating agent is not histidine.

In one embodiment, the chelating agent is not a buffer at the given pH of the composition i.e. the chelating agent does not comprise ionisable groups with $pK_a$ within 2 pH units, such as 1.5 pH units or 1 pH unit of the pH of the composition. The chelating agent, if present, is at a significantly lower concentration that the divalent metal cation. Suitably, the chelating agent when present is present at a concentration of 0.1-20 mM, such as 0.1-15 mM, 0.1-10 mM, 0.1-5 mM or 0.1-1 mM. Without being bound by theory, although perhaps counterintuitive to add a chelating agent to a composition requiring the presence of a divalent metal cation, it is thought that the presence of a chelating agent well below the concentration of the divalent metal cation may improve the chemical and/or physical stability of daptomycin, for example by eliminating trace quantities of metals cations (in particular heavy metals, e.g. $Fe^{3+}$) that are known to catalyse various degradation pathways. In one embodiment, the chelating agent is a multi-anion. By multi-anion is meant a species which has at least two anionic centres per molecule, at the particular pH of the solution. When the chelating agent is a multi-anion it may be employed as a suitable salt form (e.g. as a sodium salt), or as an acid form which forms a multi-anion in solution.

The composition may optionally comprise a polyanion. In one embodiment, the polyanion is selected from the group consisting of carboxymethyl cellulose and dextran sulfate. Suitably, the polyanion is present at a concentration of 1-10 mg/ml, such as 1-5 mg/ml.

The composition may optionally comprise a polycation. In one embodiment, the polycation is an oligomer of ethyleneimine, in particular an oligomer of ethyleneimine, wherein the number of repeating units of ethyleneimine (n) in the oligomer is in the range 2-12. In one embodiment, the polycation is an oligomer of ethyleneimine selected from the group consisting of diethylenetriamine, triethylenetetramine (TETA), tetraethylenepentamine and pentaethylenehexamine. In one embodiment, the polycation is TETA. Suitably, the polycation when present is present at a concentration of 1-10 mg/ml, such as 1-5 mg/ml.

Without being bound by theory, it is thought that the presence of polyions (i.e. polyanions and/or polycations) may improve the physical and/or chemical stability of daptomycin, for example by forming a weak complex and thus preventing interactions between daptomycin molecules that lead to aggregation.

The composition may optionally comprise a charged amphiphilic species. Such a species comprises a charged region and a non-polar (hydrophobic) region. In one embodiment, the non-polar region is a benzene ring. In another embodiment, the non-polar region is an aliphatic chain of four or more carbon atoms. In one embodiment, the charged amphiphilic species is selected from the group consisting of benzoic acid, 2-hydroxybenzoic acid, 3-hydroxybenzoic acid, 4-hydroxybenzoic acid, 3,4,5-trihydroxybenzoic acid, 4-hydroxy-3-methoxybenzoic acid, phthalic acid, isophthalic acid, terephthalic acid, 1-naphthoic acid, 2-naphthoic acid, indole-3-acetic acid, phenylacetic acid, 3-phenylpropionic acid, trans-cinnamic acid, cis-cinnamic acid and mandelic acid. In one embodiment, the charged amphiphilic species is benzoic acid, particularly in its ionic form (benzoate ion). In one embodiment, the charged amphiphilic species is not a buffer at the given pH of the composition i.e. the charged amphiphilic species does not comprise ionisable groups with $pK_a$ within 2 pH units, such as 1.5 pH units or 1 pH unit of the pH of the composition. Suitably, the charged amphiphilic species when present is present at a concentration of 1-100 mM, such as 5-20 mM; or at a concentration of 0.1-5 mM such as 0.1-4 mM, 0.1-3 mM, 0.1-2 mM or 0.1-1 mM.

Stabilizers, surfactants, antioxidants, chelating agents, polyanions, polycations and amphiphilic species which are salts but are not divalent metal cation salts, amino salts or buffer salts are included in the total concentration of one or more salts which are salts but are not divalent metal cation salts, amino salts or buffer salts in the composition.

In one embodiment the invention provides aqueous solution composition of pH in the range 6.0 to 8.0 e.g. 6.5 to 7.5 e.g. around 7.0 comprising or consisting of:
daptomycin or an analogue thereof, or a salt thereof at a concentration of >25 mg/ml up to 100 mg/ml e.g. 30-100 mg/ml, e.g. 30-60 mg/ml, e.g. 35-60 mg/ml, e.g. 40-60 mg/ml, e.g. 45-55 mg/ml, e.g. about 50 mg/ml;
a divalent metal cation at a concentration of 10-150 mM, such as 20-130 mM, 30-120 mM, 40-100 mM, 40-80 mM or 50-70 mM;
one or more salts which are not divalent metal cation salts or amino acid salts or buffer salts at a total concentration of 300 mM or more e.g. 500 mM or more e.g. around 500-3000 mM e.g. 1000-2500 mM e.g. 1500-2500 mM e.g. around 2000 mM; which formulation is substantially free of buffers.

In one embodiment the invention provides aqueous solution composition of pH in the range 6.0 to 8.0 e.g. 6.5 to 7.5 e.g. around 7.0 comprising or consisting of:
daptomycin or an analogue thereof, or a salt thereof at a concentration of e.g. >25 mg/ml up to 100 mg/ml e.g. 30-100 mg/ml, e.g. 30-60 mg/ml, e.g. 35-60 mg/ml, e.g. 40-60 mg/ml, e.g. 45-55 mg/ml, e.g. about 50 mg/ml;
a divalent metal cation at a concentration of e.g. 10-150 mM, such as 20-130 mM, 30-120 mM, 40-100 mM, 40-80 mM or 50-70 mM;
one or more salts which are not divalent metal cation salts or amino acid salts or buffer salts at a total concentration of 300 mM or more e.g. 500 mM or more e.g. around 500-3000 mM e.g. 1000-2500 mM e.g. 1500-2500 mM e.g. around 2000 mM; and
one or more buffers e.g. selected from acetate, phosphate, tris(hydroxymethyl)aminomethane (TRIS) and citrate (particularly phosphate) wherein the total concentration of buffers in the composition is 0.1-25 mM such as 0.5-20 mM e.g. 5-20 mM e.g. 5-10 mM.

In one embodiment the invention provides aqueous solution composition of pH in the range 6.0 to 8.0 e.g. 6.5 to 7.5 e.g. around 7.0 comprising or consisting of:
daptomycin or an analogue thereof, or a salt thereof at a concentration of e.g. >25 mg/ml up to 100 mg/ml e.g. 30-100 mg/ml, e.g. 30-60 mg/ml, e.g. 35-60 mg/ml, e.g. 40-60 mg/ml, e.g. 45-55 mg/ml, e.g. about 50 mg/ml;
a divalent metal cation at a concentration of e.g. 10-150 mM, such as 20-130 mM, 30-120 mM, 40-100 mM, 40-80 mM or 50-70 mM;
one or more salts which are not divalent metal cation salts or amino acid salts or buffer salts at a total concentration of 300 mM or more e.g. 500 mM or more e.g. around 500-3000 mM e.g. 1000-2500 mM e.g. 1500-2500 mM e.g. around 2000 mM; and
one or more buffers e.g. selected from acetate, phosphate, tris(hydroxymethyl)aminomethane (TRIS) and citrate (particularly phosphate) wherein the total concentration of buffers in the composition is 0.1-5 mM, such as 0.1-4 mM, 0.1-3 mM, 0.1-2 mM, 0.1-1 mM, 0.1-0.5 mM, 0.1-0.4 mM, 0.1-0.3 mM or 0.1-0.2 mM.

In one embodiment the invention provides aqueous solution composition of pH in the range 6.0 to 8.0 e.g. 6.5 to 7.5 e.g. around 7.0 comprising or consisting of:
daptomycin or an analogue thereof, or a salt thereof at a concentration of e.g. >25 mg/mi up to 100 mg/mi e.g. 30-100 mg/mi, e.g. 30-60 mg/mi, e.g. 35-60 mg/mi, e.g. 40-60 mg/mi, e.g. 45-55 mg/ml, e.g. about 50 mg/mi;
a divalent metal cation at a concentration of e.g. 10-150 mM, such as 20-130 mM, 30-120 mM, 40-100 mM, 40-80 mM or 50-70 mM;

one or more salts which are not divalent metal cation salts or amino acid salts or buffer salts at a total concentration of 300 mM or more e.g. 500 mM or more e.g. around 500-3000 mM e.g. 1000-2500 mM e.g. 1500-2500 mM e.g. around 2000 mM;

one or more buffers e.g. selected from acetate, phosphate, tris(hydroxymethyl)aminomethane (TRIS) and citrate (particularly phosphate) wherein the total concentration of buffers in the composition is 0.1-25 mM such as 0.2-20 mM such as 0.5-20 mM e.g. 5-20 mM e.g. 5-10 mM; and an uncharged tonicity modifier e.g. selected from the group consisting of glycerol, 1,2-propanediol, mannitol, sorbitol, sucrose, trehalose, lactose, PEG300 and PEG400.

In one embodiment the invention provides aqueous solution composition of pH in the range 6.0 to 8.0 e.g. 6.5 to 7.5 e.g. around 7.0 comprising or consisting of:

daptomycin or an analogue thereof, or a salt thereof at a concentration of >25 mg/ml up to 100 mg/ml e.g. 30-100 mg/ml, e.g. 30-60 mg/ml, e.g. 35-60 mg/ml, e.g. 40-60 mg/ml, e.g. 45-55 mg/ml, e.g. about 50 mg/ml;

a divalent metal cation at a concentration of 10-150 mM, such as 20-130 mM, 30-120 mM, 40-100 mM, 40-80 mM or 50-70 mM;

sodium chloride at a total concentration of 300 mM or more e.g. 500 mM or more e.g. around 500-3000 mM e.g. 1000-2500 mM e.g. 1500-2500 mM e.g. around 2000 mM; which formulation is substantially free of buffers.

In one embodiment the invention provides aqueous solution composition of pH in the range 6.0 to 8.0 e.g. 6.0 to 7.0 e.g. around 6.0 comprising or consisting of:

daptomycin or an analogue thereof, or a salt thereof at a concentration of >25 mg/ml up to 100 mg/ml e.g. 30-100 mg/ml, e.g. 30-60 mg/ml, e.g. 35-60 mg/ml, e.g. 40-60 mg/ml, e.g. 45-55 mg/ml, e.g. about 50 mg/ml;

a divalent metal cation at a concentration of 10-150 mM, such as 20-130 mM, 30-120 mM, 40-100 mM, 40-80 mM or 50-70 mM;

sodium chloride at a total concentration of 300 mM or more e.g. 500 mM or more e.g. around 500-3000 mM e.g. 1000-2500 mM e.g. 1500-2500 mM e.g. around 2000 mM; which formulation is substantially free of buffers.

In one embodiment the invention provides aqueous solution composition of pH in the range 6.0 to 8.0 e.g. 6.5 to 7.5 e.g. around 7.0 comprising or consisting of:

daptomycin or an analogue thereof, or a salt thereof at a concentration of e.g. >25 mg/ml up to 100 mg/ml e.g. 30-100 mg/ml, e.g. 30-60 mg/ml, e.g. 35-60 mg/ml, e.g. 40-60 mg/ml, e.g. 45-55 mg/ml, e.g. about 50 mg/ml;

a divalent metal cation at a concentration of e.g. 10-150 mM, such as 20-130 mM, 30-120 mM, 40-100 mM, 40-80 mM or 50-70 mM;

sodium chloride at a total concentration of 300 mM or more e.g. 500 mM or more e.g. around 500-3000 mM e.g. 1000-2500 mM e.g. 1500-2500 mM e.g. around 2000 mM; and one or more buffers e.g. selected from acetate, phosphate, tris(hydroxymethyl)aminomethane (TRIS) and citrate (particularly phosphate) wherein the total concentration of buffers in the composition is 0.1-5 mM, such as 0.1-4 mM, 0.1-3 mM, 0.1-2 mM, 0.1-1 mM, 0.1-0.5 mM, 0.1-0.4 mM, 0.1-0.3 mM or 0.1-0.2 mM.

In one embodiment the invention provides aqueous solution composition of pH in the range 6.0 to 8.0 e.g. 6.0 to 7.0 e.g. around 6.0 comprising or consisting of:

daptomycin or an analogue thereof, or a salt thereof at a concentration of e.g. >25 mg/ml up to 100 mg/ml e.g. 30-100 mg/ml, e.g. 30-60 mg/ml, e.g. 35-60 mg/ml, e.g. 40-60 mg/ml, e.g. 45-55 mg/ml, e.g. about 50 mg/ml;

a divalent metal cation at a concentration of e.g. 10-150 mM, such as 20-130 mM, 30-120 mM, 40-100 mM, 40-80 mM or 50-70 mM;

sodium chloride at a total concentration of 300 mM or more e.g. 500 mM or more e.g. around 500-3000 mM e.g. 1000-2500 mM e.g. 1500-2500 mM e.g. around 2000 mM; and one or more buffers e.g. selected from acetate, phosphate, tris(hydroxymethyl)aminomethane (TRIS) and citrate (particularly phosphate) wherein the total concentration of buffers in the composition is 0.1-5 mM, such as 0.1-4 mM, 0.1-3 mM, 0.1-2 mM, 0.1-1 mM, 0.1-0.5 mM, 0.1-0.4 mM, 0.1-0.3 mM or 0.1-0.2 mM.

In one embodiment the invention provides aqueous solution composition of pH in the range 6.0 to 8.0 e.g. 6.5 to 7.5 e.g. around 7.0 comprising or consisting of:

daptomycin or an analogue thereof, or a salt thereof at a concentration of e.g. >25 mg/ml up to 100 mg/ml e.g. 30-100 mg/ml, e.g. 30-60 mg/ml, e.g. 35-60 mg/ml, e.g. 40-60 mg/ml, e.g. 45-55 mg/ml, e.g. about 50 mg/ml;

a divalent metal cation at a concentration of e.g. 10-150 mM, such as 20-130 mM, 30-120 mM, 40-100 mM, 40-80 mM or 50-70 mM;

sodium chloride at a total concentration of 300 mM or more e.g. 500 mM or more e.g. around 500-3000 mM e.g. 1000-2500 mM e.g. 1500-2500 mM e.g. around 2000 mM;

one or more buffers e.g. selected from acetate, phosphate, tris(hydroxymethyl)aminomethane (TRIS) and citrate (particularly phosphate) wherein the total concentration of buffers in the composition is 0.1-25 mM such as 0.2-20 mM such as 0.5-20 mM e.g. 5-20 mM e.g. 5-10 mM; and an uncharged tonicity modifier e.g. selected from the group consisting of glycerol, 1,2-propanediol, mannitol, sorbitol, sucrose, trehalose, lactose, PEG300 and PEG400.

The presently claimed invention derives from the surprising observation that compositions comprising daptomycin are stabilized by the addition of divalent metal cations and high salt concentration. Such solutions may be further stabilized by minimising the buffer concentration.

Suitably the composition of the invention remains as a clear solution following storage at 2-8° C. for an extended period of time, such as at least 6 months, preferably at least 12 months, most preferably at least 18 months.

Suitably the composition of the invention remains as a clear solution following storage at 25° C. for at least 2 weeks, preferably at least 4 weeks, most preferably at least 8 weeks.

Suitably the composition of the invention has improved storage stability either at 2-8° C. or at increased temperature than in an equivalent composition that comprises higher concentration of the same buffer or buffers.

Suitably the composition of the invention has improved storage stability either at 2-8° C. or at a higher temperature e.g. 25° C. than in an equivalent composition that does not comprise divalent metal cations.

Suitably the composition of the invention has improved storage stability either at 2-8° C. or at a higher temperature e.g. 25° C. than in an equivalent composition that does not comprise one or more salts that are not divalent metal cation salts or amino acid salts or buffer salts at a total concentration of 300 mM or more.

Suitably the composition of the invention has improved storage stability either at 2-8° C. or at a higher temperature e.g. 25° C. than in an equivalent composition that does not comprise divalent metal cations and does not comprise one or more salts that are not divalent metal cation salts or amino acid salts or buffer salts at a total concentration of 300 mM or more.

In one embodiment, the composition of the invention comprises no more than 5% total impurities, such as no more than 4%, such as no more than 3%, such as no more than 2% total impurities (by total weight of daptomycin in the composition, as measured by RP-HPLC (Reversed-Phase High-Performance Liquid Chromatography) or a similar suitable technique) following storage at 2-8° C. for at least 6 months, preferably at least 12 months, most preferably at least 18 months.

In one embodiment, the composition of the invention comprises no more than 5% total impurities, such as no more than 4%, such as no more than 3%, such as no more than 2% total impurities (by total weight of daptomycin in the composition, as measured by RP-HPLC or a similar suitable technique) following storage at 25° C. for at least 2 weeks, preferably at least 4 weeks, most preferably at least 8 weeks.

In one embodiment, the composition of the invention comprises lower level of impurities than a commercially available composition comprising daptomycin (as measured by RP-HPLC or a similar suitable technique) following storage at 2-8° C. for at least 6 months, preferably at least 12 months, most preferably at least 18 months. In one embodiment, the commercially available composition is Cubicin®.

In one embodiment, the composition of the invention comprises lower level of impurities than a commercially available composition comprising daptomycin (as measured by RP-HPLC or a similar suitable technique) following storage at 25° C. for at least 2 weeks, preferably at least 4 weeks, most preferably at least 8 weeks. In one embodiment, the commercially available composition is Cubicin®.

In a further aspect of the invention, there is provided a method of improving the stability of an aqueous solution composition comprising daptomycin of pH in the range 6.0 to 8.0, which comprises adding to the composition a divalent metal cation and a high salt concentration.

In a further aspect of the invention, there is provided the use of divalent metal cations and a high salt concentration for improving the stability of an aqueous solution composition comprising daptomycin of pH in the range 6.0 to 8.0.

In an embodiment, the composition of the invention is a composition for use in therapy for example for the treatment of a gram positive bacterial infection e.g. *Staphylococcus aureus*. In an embodiment, the composition of the invention is a pharmaceutical composition.

All embodiments described above with respect to the aqueous solution composition apply equally to methods and uses of the invention.

There is also provided a container, for example made of plastics or glass, containing one dose or a plurality of doses of the composition as described herein. The container can be for example, a vial, a pre-filled syringe, a pre-filled infusion bag, or a cartridge designed to be a replaceable item for use with an injection device. In one embodiment, there is provided a vial containing a composition as described herein, suitably a 10 mL vial, suitably comprising 500 mg of daptomycin.

The compositions of the invention may suitably be packaged for injection, especially intravenous infusion or intravenous injection.

One desirable presentation of a stable liquid daptomycin formulation is a product formulated either in a vial or in a pre-filled syringe for example at a concentration of 50 mg/ml.

In some embodiments, the product will be ready to administer by IV injection without a further dilution (e.g. over a 2 minute period). Alternatively, the product will be administered by an IV infusion (e.g. a 30 minute infusion) following dilution to a required concentration. The daptomycin concentration in the diluted solution may vary depending on the indication and the patient receiving the infusion, e.g. between 0.5-10 mg/ml, e.g. 1-5 mg/ml. Compositions of the invention are hypertonic but certain compositions may nevertheless be tolerable for direct injection without dilution. Compositions of the invention with the salt concentration of about 500 mM or more, particularly, 1 M or more are suitably diluted before administration. Example diluents include water for injection, isotonic saline and isotonic dextrose solution.

Compositions of the invention are useful for the treatment of bacterial infections e.g. complicated skin and skin structure infections (cSSSI), or *Staphylococcus Aureus* bloodstream infections (bacteremia).

Compositions according to the invention are expected to have good physical and chemical stability as described herein.

EXAMPLES

Reversed-Phase Chromatography (RP-HPLC)—Method 1

Ultra-high performance reverse phase chromatography was performed using the Waters ACQUITY H-class Bio UPLC® system with a 5 μm Zorba Eclipse XDB-C18 150×4.6 mm column. Mobile Phase A (50 mM sodium phosphate in MQW) and Mobile Phase B (50% CAN, 25 mM sodium phosphate in MQW) were used in gradient elution. Injection volume was 10 μl and flow rate was 1 mL/min, with 214 nm UV detection. All analyses were performed at 60° C.

Reversed-phase chromatography (RP-HPLC)—Method 2

Ultra-high performance reverse phase chromatography was performed using the Thermo-scientific Ultimate 3000 UPLC® system with a 5 μm Kinetix C8 250×4.6 mm column. Isocratic elution was used. The mobile phase consisted of 50 mM ammonium dihydrogen phosphate in MQW, pH 5.0 (70%) and acetonitrile (30%). Injection volume was 10 μl and flow rate was 1.5 mL/min, with 214 nm UV detection. All analyses were performed at 25° C.

Example 1—Effect of Divalent Cations on the Stability of Daptomycin (50 mg/ml) at pH 6

Stability of daptomycin (50 mg/ml) was assessed using the RP-HPLC method 1 described in General Methods, following incubation at 25° C. (8 weeks) and 2-8° C. (26 weeks) of the compositions shown in Tables 1 and 2.

TABLE 1

Stability of daptomycin (50 mg/ml) following incubation at 2-8° C. for 26 weeks. RP-HPLC method 1 was used and stability is expressed as % retention of the main peak vs. time zero.

| Formulation No. | Phosphate (mM) | ADA* (mM) | Calcium chloride (mM) | Magnesium chloride (mM) | Arginine (mM) | pH | % RP-HPLC main peak (vs. time zero) 2-8° C. (26 weeks) |
|---|---|---|---|---|---|---|---|
| 1-1 | — | — | — | — | — | 6.0 | 84.62 |
| 1-2 | — | — | 30 | — | — | 6.0 | 94.98 |
| 1-3 | — | — | 60 | — | — | 6.0 | 98.98 |
| 1-4 | — | — | 120 | — | — | 6.0 | 99.91 |
| 1-5 | — | — | — | 30 | — | 6.0 | 94.08 |
| 1-6 | — | — | — | 60 | — | 6.0 | 95.74 |
| 1-7 | — | — | — | 120 | — | 6.0 | 98.01 |
| 1-8 | — | 50 | 60 | — | — | 6.0 | 96.26 |
| 1-9 | 50 | — | 60 | — | — | 6.0 | 96.00 |
| 1-10 | — | — | 60 | — | 50 | 6.0 | 97.03 |
| 1-11 | — | — | 60 | — | — | 7.0 | 98.86 |
| 1-12 | — | — | 60 | — | — | 8.0 | 95.11 |
| 1-13 | — | — | 60 | — | — | 5.0 | 93.12 |
| 1-14 | — | — | 60 | — | — | 4.0 | 81.35 |

*ADA = 2-[(2-amino-2-oxoethyl)-(carboxymethyl)amino]acetic acid.

TABLE 2

Stability of daptomycin (50 mg/ml) following incubation at 25° C. for 8 weeks. RP-HPLC method 1 was used and stability is expressed as % retention of the main peak vs. time zero.

| Formulation No. | Calcium chloride (mM) | Magnesium chloride (mM) | pH | % RP-HPLC main peak (vs. time zero) 25° C. (8 weeks) |
|---|---|---|---|---|
| 1-1 | — | — | 6.0 | 71.7 |
| 1-2 | 30 | — | 6.0 | 84.2 |
| 1-3 | 60 | — | 6.0 | 90.0 |
| 1-4 | 120 | — | 6.0 | 90.4 |
| 1-5 | — | 30 | 6.0 | 79.6 |
| 1-6 | — | 60 | 6.0 | 84.0 |
| 1-7 | — | 120 | 6.0 | 87.7 |

It was shown that the presence of calcium chloride improved the stability of daptomycin at pH 6.0. The magnitude of the improvement increased with increasing concentration of calcium in the composition. The presence of magnesium chloride also appeared to improve the stability of daptomycin in a concentration-dependent manner, although the magnitude of the improvement was lower than that brought about by calcium at the same concentration.

Interestingly, it was also demonstrated that the presence of a 50 mM buffer (phosphate or ADA) resulted in an impairment in stability in the presence of 60 mM calcium. This is in contrast with the results reported in WO2011/035108A1. Similarly, the presence of arginine at 50 mM also led to an impairment of daptomycin stability, which is in contrast with the results reported in WO2011/062676A1.

Lastly, it was shown that the optimal pH for daptomycin (50 mg/ml) stability in the presence of calcium is approximately 6.0-7.0.

Example 2—Effect of pH and Additional Formulation Parameters on the Stability of Daptomycin (50 mg/ml) in the Presence of Calcium Chloride Stability of daptomycin (50 mg/ml) was assessed using the RP-HPLC method 2 described in General Methods, following incubation at 25° C. (8 weeks) in the compositions shown in Table 3.

TABLE 3

Stability of daptomycin (50 mg/ml) following incubation at 25° C. for 8 weeks. RP-HPLC method 2 was used and stability is expressed as % retention of the main peak vs. time zero.

| Formulation No. | Calcium chloride (mM) | Sodium chloride (mM) | Glycerol (mM) | 1,2-propanediol (mM) | pH | % RP-HPLC main peak (vs. time zero) 25° C. (8 weeks) |
|---|---|---|---|---|---|---|
| 2-1 | 60 | — | — | — | 5.0 | 65.2 |
| 2-2 | 60 | — | — | — | 6.0 | 89.4 |
| 2-3 | 60 | — | — | — | 7.0 | 93.1 |
| 2-4 | 60 | — | — | — | 8.0 | 82.3 |
| 2-5 | 60 | 150 | — | — | 6.0 | 89.9 |
| 2-6 | 60 | 2000 | — | — | 6.0 | 95.9 |
| 2-7 | 60 | — | 300 | — | 6.0 | 89.1 |
| 2-8 | 60 | — | — | 300 | 6.0 | 89.2 |
| 2-9 | 60 | — | — | 2000 | 6.0 | 89.8 |

In this experiment it was shown that the pH optimum for daptomycin stability in the presence of calcium chloride is around 7.0. The stability at pH 7.0 was better than at pH 6.0 and considerably better than at pH 5.0 and 8.0. Addition of a polyol (glycerol at 300 mM or 1,2-propanediol at 300 mM and 2000 mM) had a limited impact on daptomycin stability in the presence of calcium chloride at pH 6.0. Addition of 150 mM sodium chloride also had a limited impact on daptomycin stability in the presence of calcium chloride at pH 6.0. In contrast, addition of a higher concentration (2000 mM) of sodium chloride resulted in further considerable improvement in stability of daptomycin stability in the presence of calcium chloride.

Example 3—Effect of pH and Additional Formulation Parameters on the Stability of Daptomycin (50 mg/ml) in the Presence of Calcium Chloride Stability of daptomycin (50 mg/ml) was assessed using the RP-HPLC method 2 described in General Methods, following incubation at 25° C. (8 weeks) in the compositions shown in Table 4.

TABLE 4

Stability of daptomycin (50 mg/ml) following incubation at 25° C. for 8 weeks. RP-HPLC method 2 was used and stability is expressed as % retention of the main peak vs. time zero.

| Formulation No. | Calcium chloride (mM) | Sodium chloride (mM) | pH | % RP-HPLC main peak (vs. time zero) 25° C. (8 weeks) |
|---|---|---|---|---|
| 3-1 | 60 | — | 6.0 | 92.6 |
| 3-2 | 60 | — | 6.5 | 91.2 |
| 3-3 | 60 | — | 7.0 | 88.9 |
| 3-4 | 60 | 150 | 6.0 | 92.9 |
| 3-5 | 60 | 500 | 6.0 | 93.9 |
| 3-6 | 60 | 1000 | 6.0 | 94.8 |
| 3-7 | 60 | 2000 | 6.0 | 94.9 |
| 3-8 | 60 | 150 | 7.0 | 88.8 |
| 3-9 | 60 | 500 | 7.0 | 89.6 |
| 3-10 | 60 | 1000 | 7.0 | 92.1 |
| 3-11 | 60 | 2000 | 7.0 | 93.8 |

In this experiment it was shown that the pH optimum for daptomycin stability in the presence of calcium chloride is around 6.0. The stability at pH 6.0 was better than at pH 6.5 and at pH 7.0. The results show that the stability of the formulation progressively increased as the concentration of sodium chloride was increased from 150 mM to 2000 mM.

Example 4—Effect of Buffers on the Stability of Daptomycin (50 mg/ml) in the Presence of Calcium Chloride Study A Stability of daptomycin (50 mg/ml) was assessed using the RP-HPLC method 2 described in General Methods, following incubation at 25° C. (8 weeks) in the compositions shown in Table 5.

TABLE 5

Stability of daptomycin (50 mg/ml) following incubation at 25° C. for 8 weeks. RP-HPLC method 2 was used and stability is expressed as % retention of the main peak vs. time zero.

| Formulation No. | Calcium chloride (mM) | Histidine (mM) | Sodium phosphate (mM) | ADA (mM) | PIPES (mM) | pH | % RP-HPLC main peak (vs. time zero) 25° C. (8 weeks) |
|---|---|---|---|---|---|---|---|
| 4-1 | 60 | — | — | — | — | 6.0 | 89.4 |
| 4-2 | 60 | 20 | — | — | — | 6.0 | 90.4 |
| 4-3 | 60 | — | 20 | — | — | 6.0 | 89.1 |
| 4-4 | 60 | — | — | 20 | — | 6.0 | 88.9 |
| 4-5 | 60 | — | — | — | 20 | 6.0 | 89.9 |

In this study, the presence of a buffer at a concentration of 20 mM did not appear to impact on chemical stability to a very significant effect. The formulation without buffer was very stable. It was noted that the composition containing ADA at a concentration of 20 mM contained visible particles after storage at 25° C. for 8 weeks whereas the other formulations presented in Table 5 did not show any visible particles after corresponding storage. Therefore ADA appears to impair physical stability in this composition.

Study B

A more thorough study was undertaken to investigate the effect of histidine in formulations of daptomycin. The source of daptomycin was different from that of Study A. Stability of daptomycin (50 mg/ml) was assessed using the RP-HPLC method 2 described in General Methods, following incubation at 25° C. (8 weeks) in the compositions shown in Table 6.

TABLE 6

Stability of daptomycin (50 mg/ml) following incubation at 25° C. for 8 weeks. RP-HPLC method 2 was used and stability is expressed as % retention of the main peak vs. time zero.

| Formulation No. | Calcium chloride (mM) | Histidine (mM) | pH | % RP-HPLC main peak (vs. time zero) 25° C. (8 weeks) |
|---|---|---|---|---|
| 4-6 | 60 | — | 6.0 | 92.6 |
| 4-7 | 60 | 10 | 6.0 | 91.0 |
| 4-8 | 60 | 20 | 6.0 | 88.0 |
| 4-9 | 60 | 60 | 6.0 | 84.7 |
| 4-10 | 60 | — | 7.0 | 88.9 |
| 4-11 | 60 | 10 | 7.0 | 86.7 |
| 4-12 | 60 | 20 | 7.0 | 84.3 |
| 4-13 | 60 | 60 | 7.0 | 82.1 |

This study shows that the presence of histidine buffer is deleterious to the stability of the formulation when used at a concentration of 10 mM or higher.

Taking the results of Study A and Study B together: Buffer free formulations are very stable. Histidine and ADA are generally not tolerated in the formulation and their presence appears to reduce stability. Sodium phosphate and PIPES appear to be tolerated at a concentration of up to 20 mM.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents, patent applications and references mentioned throughout the specification of the present invention are herein incorporated in their entirety by reference.

The invention embraces all combinations of preferred and more preferred groups and suitable and more suitable groups and embodiments of groups recited above.

The invention claimed is:

1. An aqueous solution composition of pH in the range 6.0 to 8.0 comprising daptomycin, an analogue thereof, or a salt thereof, at a total concentration of 30 mg/ml up to 100 mg/ml; a divalent metal cation; and a Group 1 metal halide at a total concentration of 300 mM to 2500 mM.

2. The aqueous solution composition according to claim 1, wherein the concentration of daptomycin, the analogue thereof, or the salt thereof, in the aqueous solution composition is present at a total concentration of 40 mg/ml up to 60 mg/ml.

3. The aqueous solution composition according to claim 1, wherein the aqueous solution comprises water in an amount of at least 65% (w/v) of the aqueous solution composition.

4. The aqueous solution composition according to claim 1, wherein the divalent metal cation is selected from calcium, magnesium, manganese and zinc cations.

5. The aqueous solution composition according to claim 1, wherein the divalent metal cation in the aqueous solution composition is present at a total concentration of 10-150 mM.

6. The aqueous solution composition according to claim 1, wherein the pH of the aqueous solution composition is in the range of 6.0 to 7.0.

7. The aqueous solution composition according to claim 1, wherein the halide is chloride.

8. The aqueous solution composition according to claim 1, wherein the Group I metal is sodium.

9. The aqueous solution composition according to claim 1, wherein the Group I metal halide is sodium chloride.

10. The aqueous solution composition according to claim 1, wherein the Group 1 metal halide is present at a total concentration of 400 mM to 2000 mM.

11. The aqueous solution composition according to claim 1, wherein the aqueous solution composition comprises one or more buffers comprising at least one ionizable group with a pKa in the range 4.0 to 9.0 wherein the pKa is within 2 pH units of the pH of the aqueous solution composition.

12. The aqueous solution composition according to claim 1, wherein the aqueous solution composition is substantially free of buffers.

13. The aqueous solution composition according to claim 1, further comprising an antioxidant selected from the group consisting of methionine, glutathione, ascorbate, butylated hydroquinone, lactate, nicotinamide, nicotinate, tryptophan, phenylalanine and tyrosine.

14. The aqueous solution composition according to claim 1, further comprising an amino acid selected from the group consisting of glycine, proline, methionine, arginine, lysine, aspartic acid and glutamic acid.

15. The aqueous solution composition according to claim 1, wherein the aqueous solution composition is a pharmaceutical composition for use in the treatment of bacterial infections.

* * * * *